United States Patent
Walker

(10) Patent No.: US 9,611,371 B2
(45) Date of Patent: Apr. 4, 2017

(54) PROCESS FOR EXTRACTING POLYESTER FROM AN ARTICLE

(71) Applicant: Worn Again Footwear and Accessories Limited, London (GB)

(72) Inventor: Adam Walker, London (GB)

(73) Assignee: WORN AGAIN FOOTWEAR AND ACCESSORIES, LIMITED, London (GB)

( * ) Notice: Subject to any disclaimer, the term of this patent is extended or adjusted under 35 U.S.C. 154(b) by 67 days.

(21) Appl. No.: 14/429,145

(22) PCT Filed: Sep. 23, 2013

(86) PCT No.: PCT/GB2013/052481
§ 371 (c)(1),
(2) Date: Mar. 18, 2015

(87) PCT Pub. No.: WO2014/045062
PCT Pub. Date: Mar. 27, 2014

(65) Prior Publication Data
US 2015/0232632 A1     Aug. 20, 2015

(30) Foreign Application Priority Data
Sep. 21, 2012   (GB) .................... 1216921.5

(51) Int. Cl.

| | | |
|---|---|---|
| *C08G 63/00* | (2006.01) | |
| *C08J 11/08* | (2006.01) | |
| *C07D 233/70* | (2006.01) | |
| *C07C 69/78* | (2006.01) | |
| *C07C 69/157* | (2006.01) | |
| *C07C 47/453* | (2006.01) | |
| *C07C 69/14* | (2006.01) | |
| *C08G 63/02* | (2006.01) | |

(52) U.S. Cl.
CPC ............ *C08J 11/08* (2013.01); *C07C 47/453* (2013.01); *C07C 69/14* (2013.01); *C07C 69/157* (2013.01); *C07C 69/78* (2013.01); *C07D 233/70* (2013.01); *C08J 2367/02* (2013.01)

(58) Field of Classification Search
CPC .................................................... C08J 2367/02
USPC .......................................................... 521/48
See application file for complete search history.

(56) References Cited

U.S. PATENT DOCUMENTS

2005/0027023 A1*   2/2005   Masuda .................. C07C 67/03
                                                                521/48

FOREIGN PATENT DOCUMENTS

| JP | S6254735 A | 3/1987 |
| JP | 2004308077 | * 11/2004 |

OTHER PUBLICATIONS

European Examination Report, Application No. EP 13770964.8, dated Dec. 14, 2016.

* cited by examiner

Primary Examiner — Terressa Boykin
(74) Attorney, Agent, or Firm — MacMillan, Sobanski & Todd, LLC

(57) ABSTRACT

A process for extracting polyester from an article using a solvent system using a compound according to Formula I is described, where

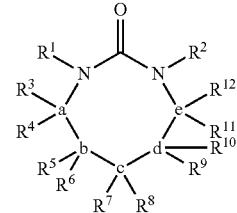

Formula I wherein $R_1$ and $R_2$ are each independently selected from: hydrogen, alkyl, alkenyl, alkynyl, aryl or alkoxy groups; $R_3$ to $R_{12}$ are each independently selected from: hydrogen, alkyl, alkenyl, alkynyl, aryl or alkoxy groups; and each of "a" to "e" is a carbon atom, wherein the total linear chain length of a-b-c-d-e is in the range of 2 to 5 carbons.

19 Claims, No Drawings

PROCESS FOR EXTRACTING POLYESTER FROM AN ARTICLE

The present invention claims the benefit of the PCT/GB2013/052481 filed 23 Sep. 2013, which claims priority to GB/1216921.5 filed 21 Sep. 2012.

FIELD OF INVENTION

The invention relates to a process and use of a compound for extracting polymers from articles, in particular polyesters, using a solvent system.

BACKGROUND TO THE INVENTION

Synthetic polymers are found in a wide range of products in almost every industry. A common family of polymers used in products, particularly in the packaging and clothing industries, are polyesters. Polyesters are polymers that comprise an ester functionality (—COO—) in the polymer backbone.

Although some polyesters can exhibit good biodegradability, such as naturally occurring compounds like cutin, most synthetic polyesters are usually energetically expensive to break down and therefore are often discarded rather than recycled, contributing to waste.

Current techniques for recycling polyester usually involve energy intensive processes and/or harsh chemical conditions in order to reduce the polymer back to its component monomers. Another approach taken to recycle polyester, is to mechanically break down polyester products. This retains the chemical structure of the polymers and the resulting polyester fragments can be reformed into a useful source of polymer, such as pellets for yarn, for example via a heat treatment process.

However, both these processes typically require high temperatures, are energy intensive and often require harsh chemical agents. Further, whilst many thermosoftening polyesters can be remoulded with heating, this is not true for many thermosetting polyesters. Therefore, what is required is a simple system for recycling polyester from waste products that is energy efficient and avoids the use of harsh chemical reagents.

The invention is intended to overcome or ameliorate at least some of these problems.

SUMMARY OF INVENTION

There is provided in a first aspect of the invention, a process for extracting polyester from an article using a solvent system comprising a compound according to any of general Formula I to VI

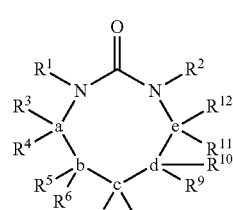

Formula I

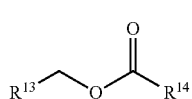

Formula II

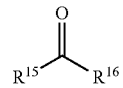

Formula III

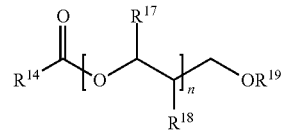

Formula IV

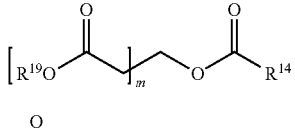

Formula V

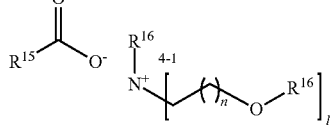

Formula VI wherein $R_1$ and $R_2$ are each independently selected from: hydrogen, alkyl, alkenyl, alkynyl, aryl or alkoxy groups; $R_3$ to $R_{12}$ are each independently selected from: hydrogen, alkyl, alkenyl, alkynyl, aryl or alkoxy groups; X is selected from O or S; and each of a to e is a carbon atom, wherein the total linear chain length of a-b-c-d-e is in the range of 2 to 5 carbons; $R^{13}$ and $R^{15}$ are both independently aryl groups; $R^{14}$, $R^{16}$, $R^{17}$, $R^{18}$ and $R^{19}$ are each independently selected from hydrogen, alkyl, alkenyl, alkynyl or aryl groups; n is an integer in the range of 1 to 8; m is 3; and l is an integer in the range of 1 to 3; or combination thereof.

The inventors have surprisingly found, through extensive experimentation, that the above compounds are particularly effective at dissolving polyesters. Further, these compounds are less damaging to the environment compared to many of the current industry standard chemicals. Further, extraction of polyesters can be performed using these solvents alone or in combination with one another and other solvents, at the temperatures described herein.

The term "solvent system" is intended to mean a homogeneous or heterogeneous combination of one or more solvents. These solvents may or may not be miscible with one another. The compounds according to general formulae I to VI display low toxicity and have been found by the inventors to be effective at dissolving and subsequently precipitating polyesters over an energy efficient temperature range. Dissolution of the polyester has several advantages over existing mechanical methods, including ease of separation of common impurities. Dyes and embedded microparticles are frequently not soluble in the solvent system of the invention and are therefore easy to separate using techniques known to the skilled person.

Typically, the article from which the polyester is extracted is a fabric. The term "fabric" is intended to mean any material comprising a matrix of woven and/or non-woven fibers. A "polyester fabric" is intended to mean a fabric in which at least one of the fibers contains polyester. Fabrics are included in a range of consumer products, such as furniture and clothing, and a great deal of fabric is frequently discarded along with the associated product. As such, the invention allows polyester to be readily extracted from these fabrics in a cost effective manner which would otherwise simply be disposed of akin to conventional waste.

It is often the case that the article is clothing. The term "clothing" is intended to encompass all forms of apparel. Most clothing is used regularly and is washed frequently. This typically causes clothing to become damaged and no longer useable more quickly than other products containing fabric. In view of the low cost to manufacture polyester clothing, the expense of conventional recycling techniques and high demand for new clothing (for example from the fashion industry), the established practice in the art is to simply dispose of waste clothing with conventional rubbish although energetic recycling techniques have been used.

In another embodiment, the articles from which polyesters are extracted may included packaging materials such as the plastics used to contain and wrap food products. Plastic bottles and drinks containers are also articles which are suitable for use with the process of the invention.

The polyester described in the invention is not particularly limited. Typically, the polyester will be selected from: polyglycolic acid (PGA), polylactic acid (PLA), polycaprolactone (PCL), polyethylene adipate (PEA), polyhydroxylkanoate (PHA), polyethylene terephthalate (PET), polybutylene terephthalate (PBT), polytrimethylene terephthalate (PTT), polyethylene naphthalate (PEN) or combination thereof. It is often the case that the polyester is selected from: polyglycolic acid (PGA), polylactic acid (PLA), polyethylene terephthalate (PET) and even more typically, the polyester is polyethylene terephthalate (PET).

The solvent system used in the invention may be a heterogeneous system comprising two or more immiscible solvents. One of the solvents is typically selected to dissolve polyester and comprises a compound according to any of general formulae I to VI or combination thereof, whilst the other solvent or solvents are typically selected to dissolve other common substances found in the article to be dissolved. In use, the heterogeous system is typically agitated in order to create a uniform mixture and an article is exposed to the mixture. After a period of time, the agitation is halted and the solvent system is allowed to separate and one or more of the immiscible solvent phases can be extracted.

Alternatively, the solvent system used in the invention may be a homogeneous system and the solvent system may comprise one or more compounds according to any of general formulae I to VI or combinations thereof in an amount in the range of 30% to 100% by mass of the total mass of the solvent system. This upper limit of 100%, is intended to mean 'practically 100%' or '99% or 98%' as, in real world situations, it is never possible to obtain absolute purity. Typically, the solvent system may comprise one or more compounds according to any of general formulae I to VI or combinations thereof in an amount of at least 50% by mass of the total mass of the solvent system. Even more typically, the solvent system may comprise one or more compounds according to any of general formulae Ito VI or combinations thereof in an amount of at least 55%, 60%, 65%, 70%, 75%, 80%, 85%, 90% or 95% by mass of the total mass of the solvent system so, in the range of 50%-100%, 55%-100%, 60%-100%, 65%-100%, 70%-100%, 75%-100%, 80%-100%, 85%-100%, 90%-100% or 95%-100% by mass of the total mass of the solvent system.

In one example of the invention, the solvent system may be heated. This encourages polyester to dissolve in the solvent system. Usually, the solvent is heated to a temperature in the range of 50° C. to 150° C., or more typically in the range of 60° C. to 130° C., or even more typically in the range of 70° C. to 110° C. These temperatures maximise the amount and rate of dissolution of polyester whilst minimising the energy required to raise and sustain the temperature of the solvent system. Once a sufficient quantity of polyester has been dissolved, the solvent system may be separated and can be cooled to precipitate the polyester.

Whilst there is no particular restriction on the period of time that an article is exposed to the solvent system of the present invention, this period may be in the range of 30 minutes to 4 hours, more typically in the range 45 minutes to 3 hours, or even more typically in the range 1 to 2 hours. These durations minimise the amount of time required to dissolve a sufficient proportion of the polyester against the energy required to sustain the temperature of the solvent system of said period of time.

The process is usually conducted at atmospheric pressure. The process can be conducted under pressurised conditions, in order to achieve superheated a solvent system with higher temperatures than those available at standard pressure and therefore faster rates of reaction. However, this often requires specific reaction chambers capable of withstanding high pressure and intensive heating. This requires a greater input of energy and does not usually improve the energy efficiency of the process.

The term 'alkyl' is intended to encompass aliphatic, linear and cyclic saturated carbon chains as well as branched saturated carbon chains. Typically, the alkyl groups used in the invention are between $C_1$ to $C_{10}$, more typically between $C_1$ to $C_8$ and even more typically $C_1$ to $C_5$. The term 'aryl' is intended to refer to an aromatic ring structure. This may include one or more fused rings and the ring or rings may each independently be 5-, 6-, 7-, 8- or 9-membered rings. Typically, the aryl groups will be a single aromatic ring and even more typically, the ring may be a 5-, or 6-membered ring.

The term 'alkenyl' is intended to refer to linear or cyclic carbon chains as well as branched carbon chains having at least one unsaturated carbon-carbon double bond. Typically, the alkenyl groups used in the invention are between $C_1$ to $C_{10}$, more typically between $C_1$ to $C_8$ and even more typically $C_1$ to $C_5$. The term 'alkynyl' is intended to refer to linear or cyclic carbon chains as well as branched carbon chains having at least one unsaturated carbon-carbon triple bond. Typically, the alkynyl groups used in the invention are between $C_1$ to $C_{10}$, more typically between $C_1$ to $C_8$ and even more typically $C_1$ to $C_5$.

The term 'alkoxy' is intended to mean an alkyl group as defined above, which is bonded to one of the nitrogen atoms or one of groups a to e of general formula I or is bonded to the compounds according to general formulae II to VI via an ether linkage.

In general formula I, $R_1$ and $R_2$ may each be independently selected from: hydrogen, alkyl, aryl, alkenyl, alkynyl and alkoxy groups, although more typically, $R_1$ and $R_2$ may each be independently hydrogen or an alkyl group, such as a methyl, ethyl or n-propyl group. It is often the case that $R_1$ and $R_2$ are each independently hydrogen or a methyl group and it may be that $R_1$ and $R_2$ are both methyl groups. Compounds having this combination of groups are not only comparatively low in terms of toxicity and cost to synthesise, but also provide a compound having excellent solubility to polyester.

It is typically the case that X is O. Oxygen is typically used rather than sulphur as the precursors used to make the oxygen containing species are easier to handle, less hazardous and the oxygen containing compound is more stable than the sulphur analogue. The five membered ring is also often used as the synthetic route is less complex and this compound demonstrates optimum solubility towards polyesters compared to the six and seven membered analogues.

The total linear chain length of a-b-c-d-e is in the range of 2 to 5, often 2 to 4 carbons. Even more typically, the total linear chain length of a-b-c-d-e is in the range of 2 to 3 carbons, and more typically still the total linear chain length of a-b-c-d-e is 2 carbons. So, for instance, in a five membered ring, a and b could arbitrarily be present, and c, d and e arbitrarily absent Although each of a to e are equivalent in terms of possible substituents, and the identifers a to e and $R_3$ to $R_{12}$ allow for the independent substitution of each ring carbon with each of the options for substituent as defined above. Accordingly, the total ring size may be five membered (2 carbons, for instance a and b present and c, d and e absent), six membered (3 carbons, for instance a-c present and d and e absent), seven membered (4 carbons, for instance a-d present and e absent) or eight membered (all of a-e present). However, as described above often the ring will be five or six membered, often five membered.

Each of $R_3$ to $R_{12}$ may be independently selected from hydrogen, alkyl, alkenyl, alkynyl, aryl and alkoxy groups. Often $R_3$ to $R_{12}$ may also often be alkyl, particularly short chain alkyl such as methyl, ethyl or n-propyl. Often, each carbon will carry only one substituent, so that on each carbon one of the R groups will be H. For instance, for a, $R_3$ may be hydrogen and $R_4$ selected from alkyl, alkenyl, alkynyl, aryl and alkoxy groups. Similar patterns may be found for b, with $R_5$ and $R_6$, c with $R_7$ and $R_8$, d with $R_9$ and $R_{10}$, and e with $R_{11}$ and $R_{12}$.

Often one or more of a-e will have the associated R groups as H, so that not all ring carbon atoms are substituted. For instance, $R_3$ and/or $R_4$ may be selected from alkyl, alkenyl, alkynyl, aryl and alkoxy but the others of $R_5$-$R_{12}$ may be H. Having only one substituent (R≠H) on some or all carbon atoms and/or having substituents on some carbon atoms only, ensures that solubility is retained.

In general formulae II to VI it is typically the case that $R^{13}$ and $R^{15}$ are each independently phenyl groups and typically $R^{14}$, $R^{16}$, $R^{17}$, $R^{18}$ and $R^{19}$ are each independently hydrogen or an alkyl group wherein $R^{14}$, $R^{16}$, $R^{17}$, $R^{18}$ and $R^{19}$ may each independently be a $C_1$ to $C_4$ alkyl group. The integer n is typically selected to be 1, 2 or 3 and it is often the case that 1 is 3.

Usually, the solvent system of the present invention comprises one or more compounds selected from: dimethylimidazolidinone, benzyl acetate, benzyl benzoate, benzaldehyde, dipropyl glycol methyl ethyl acetate, diethyl glycol butyl ether acetate, propylene glycol benzyl ether acetate, acetyl tributyl citrate, tris(2-methylethoxy) ethyl ammonium benzoate, or combinations thereof.

The process may further comprise a separation step. The separation step typically comprises cooling of the whole or part of the solvent system to precipitate the dissolved polyester, usually followed by filtration. Once the polyester has been dissolved it is desirable to recover the polyester and convert it into a re-useable form. Typically, the precipitate is washed to remove any impurities and any solvent residue. The precipitate is typically dried under vacuum and may be heated to encourage removal of residual solvent. These additional steps ensure that the precipitated polyester is substantially free from impurities and suitable for forming into usable polyester.

Once the precipitate has been washed and dried, this 'raw' polyester is typically moulded into pellets and/or converted into fibres. This may be performed by heating and/or shaping the 'raw' polyester.

In a second aspect of the invention, there is provided use of a composition comprising one or more compounds according to any of general formulae I to VI or combinations thereof for extracting polyester from an article. Typically, the article from which the polyester is extracted is an article comprising a fabric and it is fabric which is treated. Even more typically the fabric is clothing. Alternatively, the article may be a packaging material which may include plastic bottles.

The inventors have surprisingly found that many of the compounds according to general formulae I to VI display similar physical properties, despite the differences in chemical functionality and that each performs well at dissolving polyesters, particularly PET.

Unless otherwise stated each of the integers described in the invention may be used in combination with any other integer as would be understood by the person skilled in the art. Further, although all aspects of the invention preferably "comprise" the features described in relation to that aspect, it is specifically envisaged that they may "consist" or "consist essentially" of those features outlined in the claims. In addition, all terms, unless specifically defined herein, are intended to be given their commonly understood meaning in the art.

Further, in the discussion of the invention, unless stated to the contrary, the disclosure of alternative values for the upper or lower limit of the permitted range of a parameter, is to be construed as an implied statement that each intermediate value of said parameter, lying between the smaller and greater of the alternatives, is itself also disclosed as a possible value for the parameter.

In addition, unless otherwise stated, all numerical values appearing in this application are to be understood as being modified by the term "about".

The invention will be described with reference to the following examples.

EXAMPLES

Example 1

Poly(ethylene terephthalate) (PET) (Sigma-Aldrich, >99%, 3.0 g) was added to 40 mL of 1,3-dimethylimidazolidinone (DMI) (Sigma-Aldrich, >98%) in a 250 mL glass beaker on a hotplate held at 80° C. The mixture was heated to 95° C. for 2 hours, after which it was removed from the heat and hot filtered to yield 0.26 g of undissolved solid. The hot solution began to gelatinize at approximately 50° C. and after cooling to room temperature gradually separated into a liquid phase and a solid gelatinous phase. The phases were separated by conventional filtration and the filter cake was washed with 25 mL acetone followed by three washes each of 25 mL deionized water. The resultant damp white solid (4.2 g) was collected, transferred to a vacuum desiccator over silica gel and dried to constant weight to yield 2.42 g (81% yield) of a powdery white solid whose infra-red spectrum correlated with that of virgin poly(ethylene terephthalate).

Example 2

A sample of a white polyester shirt (17.75 g) was cut into 1 cm² squares and added to 80 mL of 1,3-dimethylimidazolidinone (DMI) in a 500 mL glass beaker on a hotplate held at 80° C. The mixture was heated to 95° C. with occasional stirring to prevent localized decomposition of polymer at surface "hot spots". After 1 hour, the mixture was removed from the heat and hot filtered to yield 4.3 g of undissolved solid. The hot solution began to gelatinize at approximately 50° C. and after cooling to room temperature gradually separated into a liquid phase and a solid gelatinous phase. The phases were separated by conventional filtration and the filter cake was washed with 25 mL acetone followed by three washes each of 25 mL deionized water. The resultant damp white solid (17.59 g) was collected, transferred to a vacuum desiccator over silica gel and dried to constant weight to 13.1 g (74% yield) of a powdery white solid whose infra-red spectrum correlated with that of virgin poly(ethylene terephthalate).

Example 3

Dissolution of PET in Butyl Benzoate

To 200mL butyl benzoate at 100° C. was added, with stirring, 25 g shredded textile (60 wt. % poly(ethylene terephthalate), 40 wt. % cotton). The mixture was stirred with heating for 2 hours. At the conclusion of this period, solid material was filtered off and the hot filtrate was collected and cooled to room temperature, whereupon a quantity of white solid precipitate formed. The filtrate was diluted with 200 mL isopropyl alcohol and filtered using a Buchner funnel. The resultant white solid was washed with a further 100 mL isopropyl alcohol followed by 200 mL deionized water and dried to constant weight in a vacuum desiccator to yield 4 g (26% yield) of crystalline powdery solid, mp 253-256° C.

Example 4

Dissolution of PET in Butyl Benzoate

To 200 mL butyl benzoate at 100° C. was added, with stirring, 25 g shredded textile (60wt. % poly(ethylene terephthalate), 40 wt. % cotton). The mixture was stirred with heating for 2 hours. At the conclusion of this period, solid material was filtered off and the hot filtrate was collected and cooled to room temperature, whereupon a quantity of white solid precipitate formed. The filtrate was diluted with 200 mL isopropyl alcohol and filtered using a Buchner funnel. The resultant white solid was washed with a further 100 mL isopropyl alcohol followed by 200 mL deionized water and dried to constant weight in a vacuum desiccator to yield 4 g (26% yield) of crystalline powdery solid, mp 253-256° C.

Example 5

Dissolution of PET in Benzyl Acetate

To 25 mL benzyl acetate at 100° C. was added, with stirring, 2.5 g shredded textile (60 wt. % poly(ethylene terephthalate), 40 wt. % cotton). The mixture was stirred with heating for 2 hours. At the conclusion of this period, solid material was filtered off and the hot filtrate was collected and cooled to room temperature, whereupon a quantity of white solid precipitate formed. The solid was collected by vacuum filtration and washed with 25 mL isopropyl alcohol followed by 50 mL deionized water. The solid residue was dried to constant weight in a vacuum desiccator over $P_2O_5$ to yield 0.85 g (57% yield) of white powder, mp 262-266° C.

Example 6

Dissolution of PET in Benzaldehyde

To 25 mL benzaldehyde at 90° C. was added, with stirring, 2.5 g shredded textile (60 wt. % poly(ethylene terephthalate), 40 wt. % cotton). The mixture was stirred with heating for 2 hours. At the conclusion of this period, solid material was filtered off and the hot filtrate was collected and cooled to room temperature, whereupon a quantity of white solid precipitate formed. The solid was collected by vacuum filtration and washed with 25 mL industrial methylated spirits followed by 50 mL deionized water. The solid residue was dried to constant weight in a vacuum desiccator over $P_2O_5$ to yield 0.71 g (47% yield) of white powder, mp 260-265° C.

Example 7

Dissolution of PET in Dipropylene Glycol Methyl Ether Acetate

To 25 mL dipropylene glycol methyl ether acetate at 90° C. was added, with stirring, 2.5 g shredded textile (60 wt. % poly(ethylene terephthalate), 40 wt. % cotton). The mixture was stirred with heating for 2 hours. At the conclusion of this period, solid material was filtered off and the hot filtrate was collected and cooled to room temperature, whereupon a small quantity of white solid precipitate formed. The solid was collected by vacuum filtration and washed with 25 mL industrial methylated spirits followed by 50 mL deionized water. The solid residue was dried to constant weight in a vacuum desiccator over $P_2O_5$ to yield 0.22 g (15% yield) of white powder, mp 262-265° C.

Example 8

Dissolution of PET in Propylene Glycol Benzyl Ether Acetate

To 25 mL dipropylene glycol methyl ether acetate at 100° C. was added, with stirring, 2.5 g shredded textile (60 wt. % poly(ethylene terephthalate), 40 wt. % cotton). The mixture was stirred with heating for 2 hours. At the conclusion of this period, solid material was filtered off and the hot filtrate was collected and cooled to room temperature, whereupon a small quantity of white solid precipitate formed. The solid was collected by vacuum filtration and washed with 25 mL isopropyl alcohol followed by 50 mL deionized water. The solid residue was dried to constant weight in a vacuum desiccator over $P_2O_5$ to yield 0.58 g (39% yield) of off-white powder, mp 254-259° C.

The invention claimed is:

1. A process for extracting polyester from an article using a solvent system comprising a compound according to Formula I

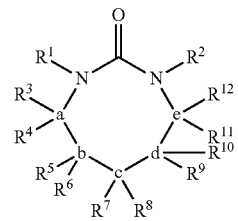

Formula I wherein $R_1$ and $R_2$ are each independently selected from: hydrogen, alkyl, alkenyl, alkynyl, aryl or alkoxy groups;

$R_3$ to $R_{12}$ are each independently selected from: hydrogen, alkyl, alkenyl, alkynyl, aryl or alkoxy groups;

and each of a to e is a carbon atom, wherein the total linear chain length of a-b-c-d-e is in the range of 2 to 5 carbons.

2. A process according to claim 1, wherein the article is fabric.

3. A process according to claim 1, wherein the article is clothing.

4. A process according to claim 1, wherein the article is plastics bottles.

5. A process according to claim 1, wherein the polyester is selected from: Polyglycolic acid (PGA), Polylactic acid (PLA), Polycaprolactone (PCL), Polyethylene adipate (PEA), Polyhydroxyalkanoate (PHA), Polyethylene terephthalate (PET), Polybutylene terephthalate (PBT), Polytrimethylene terephthalate (PTT), Polyethylene naphthalate (PEN) or combination thereof.

6. A process according to a claim 5, wherein the polyester is polyethylene terephthalate.

7. A process according to claim 1, wherein the solvent system is homogeneous.

8. A process according to claim 1, wherein the solvent system comprises one or more compounds according to Formula I in an amount in the range 30% to 100% by mass of the total mass of the composition.

9. A process according to claim 8, wherein the solvent system comprises one or more compounds according to Formula I in an amount of at least 90% by mass of the total mass of the solvent system.

10. A process according to claim 1, wherein the solvent system has a temperature in the range of 70° C. to 110° C.

11. A process according to claim 1, wherein the article is exposed to the solvent system for a period of time in the range of 1 to 2 hours.

12. A process according to claim 1, wherein $R_1$ and $R_{12}$ are each independently hydrogen or an alkyl group.

13. A process according to claim 12, wherein $R_1$ and $R_2$ are both methyl groups.

14. A process according to claim 12, $R_3$ to $R_{12}$ are hydrogen.

15. A process according to claim 1, wherein the total linear chain length of a-b-c-d-e is 2 carbons.

16. A process according to claim 1, further comprising a separation step adapted to remove dissolved polyester from the whole or part of the solvent system.

17. A composition comprising one or more compounds according to Formula I, for extracting polyester from an article, wherein the Formula I comprises

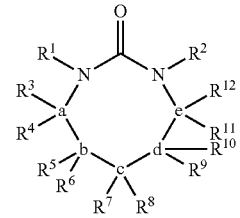

Formula I wherein $R_1$ and $R_2$ are each independently selected from: hydrogen, alkyl, alkenyl, alkynyl, aryl or alkoxy groups;

$R_3$ to $R_{12}$ are each independently selected from: hydrogen, alkyl, alkenyl, alkynyl, aryl or alkoxy groups;

and each of a to e is a carbon atom, wherein the total linear chain length of a-b-c-d-e is in the range of 2 to 5 carbons.

18. A composition according to claim 17, wherein the article is a fabric.

19. A composition according to claim 18, wherein the article is clothing.

* * * * *